United States Patent [19]

Briggs et al.

[11] Patent Number: 5,457,023
[45] Date of Patent: Oct. 10, 1995

[54] NON-IONIC SURFACE ACTIVE COMPOUNDS

[75] Inventors: Catherine B. Briggs, Harrow; Ian M. Newington, High Wycombe; Alan R. Pitt, St. Albans, all of United Kingdom

[73] Assignee: Eastman Kodak Company, Rochester, N.Y.

[21] Appl. No.: 170,562

[22] Filed: Dec. 20, 1993

[30] Foreign Application Priority Data

Dec. 19, 1992 [GB] United Kingdom ............ 9226496

[51] Int. Cl.⁶ .................................................. G03C 1/38
[52] U.S. Cl. ........................ 430/631; 430/638; 430/628; 430/640; 430/641; 430/643
[58] Field of Search ....................... 430/631, 637, 430/638, 640–643, 628

[56] References Cited

FOREIGN PATENT DOCUMENTS

| | | |
|---|---|---|
| 0312087 | 10/1988 | European Pat. Off. . |
| 314425 | 10/1988 | European Pat. Off. ............... 430/631 |
| 0541467 | 11/1992 | European Pat. Off. . |
| WO92/15554 | 3/1991 | WIPO . |

OTHER PUBLICATIONS

Chemical Abstracts, vol. 82, 1975 (CA82(11):73363y).

*Primary Examiner*—Thorl Chea
*Attorney, Agent, or Firm*—Andrew J. Anderson

[57] ABSTRACT

A water-soluble or water-dispersible, non-ionic surface active compound is provided having the formula

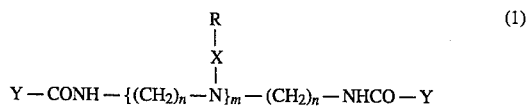

wherein each Y independently is a hydrophilic polyhydroxyalkyl group;

each X independently is

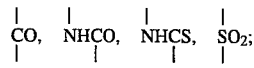

each R independently is a hydrophobic substituted or unsubstituted alkyl group or a hydrophobic substituted or unsubstituted aryl group;

each n independently is an integer from 2 to 6; and, each m is an integer from 2 to 4.

Such surfactants can be used in hydrophilic colloid compositions in the manufacture of photographic materials.

9 Claims, No Drawings

NON-IONIC SURFACE ACTIVE COMPOUNDS

FIELD OF THE INVENTION

The invention relates to non-ionic surface active compounds.

1. Background of the Invention

Many non-ionic surface active compounds are known. A small proportion of these compounds are suitable as coating aids or dispersing aids in the preparation of photographic materials. For example, EP-A-0 314 425 describes surface active agents comprising two hydrophilic polyhydroxyalkyl chains and two hydrophobic hydrocarbon chains.

2. Problem to be solved by the Invention

There is a need for alternative non-ionic surface active compounds which can be used as wetting aids, emulsifiers, dispersing aids, coating aids, modifiers of rheology of disperse systems stabilized by ionic surfactants or polymeric surfactants.

Problems associated with the known compounds identified above which are suitable for use in the manufacture of photographic materials include a lack of ease of synthesis and a lack of biodegradability.

Another problem associated with some known single hydrophobic chain sugar-based surfactants is lack of dispersibility or lack of solubility in water.

SUMMARY OF THE INVENTION

The invention provides a water-soluble or water-dispersible, non-ionic surface active compound having the formula

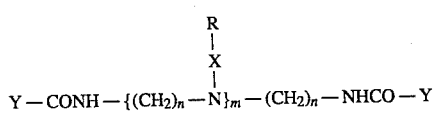

(1)

wherein each Y independently is a hydrophilic polyhydroxyalkyl group;

each X independently is

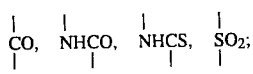

each R independently is a hydrophobic substituted or unsubstituted alkyl group or a hydrophobic substituted or unsubstituted aryl group;

each n independently is an integer from 2 to 6; and, each m is an integer from 2 to 4.

In another aspect, the invention provides a coating composition comprising a hydrophilic colloid and a surface active compound according to formula (1) above.

The invention also provides a photographic material comprising a support having thereon at least one layer comprising a hydrophilic colloid and a surface active compound according to formula (1) above.

ADVANTAGEOUS EFFECT OF THE INVENTION

Surface active compounds in accordance with the invention are more easily synthesized and are more biodegradable than the prior art compounds identified above. Also, the compounds are more dispersible or soluble in water than some sugar-based surfactants with a single hydrophobic chain.

DETAILED DESCRIPTION OF THE INVENTION

Preferred compounds include those wherein each Y is $-(CHOH)_yCH_2OH$ in which y is an integer from 3 to 5. Preferably, y is 4.

Preferred compounds include those wherein each X is $-CO-$.

Preferred compounds include those wherein the total number of carbon atoms in the R groups does not exceed 24. Preferably, each R group is an alkyl group having from 4 to 20 carbon atoms. Preferably, the total number of carbon atoms in the alkyl groups is from 12 to 18. Preferred compounds include those wherein the R groups are substituted with one or more fluorine atoms.

Preferred compounds include those wherein n is 2 or 3.

Preferred compounds include those wherein m is 2.

A particularly preferred group of compounds is that wherein each Y is $-(CHOH)_4CH_2OH$, each X is $-CO-$, each R is an alkyl group having from 7 to 9 carbon atoms, each n is 2 and m is 2.

The compounds of the invention can be prepared by reacting together (a) a polyalkyleneamine having the formula $H_2N\{(CH_2)_n-NH\}_m-(CH_2)_n-NH_2$, (b) a polyhydroxyalkyl ester and (c) a substituted or unsubstituted alkyl or aryl carboxylic acid derivative, isocyanate, isothiocyanate or sulphonyl halide in the appropriate molar ratios. An example of a suitable reactive carboxylic acid derivative is a mixed anhydride.

The reactions can be carried out in solution using an organic solvent such as dimethylformamide (DMF) at a temperature from 20° to 80° C.

(a) and (b) can be reacted together and the intermediate product isolated before subsequent reaction with (c) (Method A).

Alternatively, (a) and (b) can be reacted together and subsequently (c) can be added without isolation of the intermediate product (Method B).

The compounds of the invention may be used as emulsifying agents. For example, stable oil-in-water emulsions can be prepared by mixing the oil and water together in the presence of a compound of the invention. Examples of oils which can be emulsified in this way include hydrocarbons such as dodecane and pentadecane.

The compounds of the invention may be used as coating aids in aqueous hydrophilic colloid compositions e.g. a gelatin solution. In a particular application, the compounds may be used in the preparation of light sensitive photographic materials. Such a material comprises a support having thereon at least one layer comprising a hydrophilic colloid and a compound of the invention.

In the preparation of a photographic material, it is usual to coat a support with one or more layers comprising an aqueous solution of a hydrophilic colloid binder e.g. gelatin. Such layers include, for example, silver halide emulsion layers, intermediate layers, antihalation layers, filter layers, antistatic layers and protective layers. For multilayer materials, the layers may be coated simultaneously on conventional photographic supports as described in U.S. Pat. Nos. 2,761,791 and 3,508,947.

In producing the thin hydrophilic colloid layers of such photographic materials, it is required that coating solutions are coated uniformly without the formation of repellency spots or craters, hereinafter referred to as repellencies. A repellency is a round, oval-shaped or comet-shaped indentation or crater in the layer or one or more of the layers coated and is usually produced by the presence of small particles or droplets of insoluble materials in the form of addenda, impurities or contaminants which are in contact with the uppermost liquid-air interface of the coated layer(s) and have surface activity (i.e. are capable of reducing the surface tension of the liquid-air interface during the coating process).

Solutions coated in the preparation of photographic materials often contain dispersed, insoluble photographic addenda, which might include organic solvents, or addenda to alter certain physical properties, which might include lubricants, each of which may be capable of imparting repellencies to the coated layer(s). Even photographic gelatin may contain insoluble residues of naturally-occurring animal fats and fatty acids which are capable of imparting repellencies to the coated layer(s). Also, surface active contaminants may originate from external sources during the preparation of the coating composition or during coating. For example, the layer(s) being coated, or immediately after coating, may be unintentionally showered by droplets of lubricating oils used in the apparatus.

In one aspect of the invention, a surface active compound of the invention is used as a coating aid in the formation of a hydrophilic colloid layer. Preferably, the coating aid is used in an amount from 0.01 to 0.30, more preferably from 0.05 to 0.20, weight % based on the weight of the hydrophilic colloid coating composition. The range of concentration within which the coating aid is used depends on the source of repellency. It also depends on whether other surface active agents are present.

Being non-ionic, the surface active compounds of the invention do not cause increases in viscosity when added to charged polyelectrolyte systems. In fact, they actually lower viscosity when added to aqueous complexes of ionic surfactant and gelatin. If an oil dispersion is also present in the complex mixture, the lowering of viscosity is particularly effective at low shear. Thus, the surface active compounds of the invention may be used advantageously in combination with an ionic surfactant e.g. an anionic surfactant.

The preferred hydrophilic colloid is gelatin e.g. alkali-treated gelatin (cattle bone or hide gelatin) and acid-treated gelatin (pigskin gelatin) or a gelatin derivative e.g. acetylated gelatin and phthalated gelatin. Other suitable hydrophilic colloids include naturally occurring substances such as proteins, protein derivatives, cellulose derivatives e.g. cellulose esters, polysaccharides e.g. dextran, gum arabic, zein, casein and pectin, collagen derivatives, agar-agar, arrowroot and albumin. Examples of suitable synthetic hydrophilic colloids include polyvinyl alcohol, acrylamide polymers, maleic acid copolymers, acrylic acid copolymers, methacrylic acid copolymers and polyalkylene oxides.

In the following discussion concerning the nature of photographic materials, reference will be made to Research Disclosure, December 1978, Item 17643, published by Industrial Opportunities Ltd., The Old Harbourmaster's, 8 North Street, Emsworth, Hants P010 7DD, U.K. This publication will be identified hereafter as "Research Disclosure".

The photographic material may comprise a negative-working or positive-working silver halide emulsion layer. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

For color photographic materials, references giving information on couplers and on methods for their dispersions are given in Sections VII and XIV, respectively, of Research Disclosure. An account of dye-forming development is given in 'Modern Photographic Processing', Vol. 2, Grant Haist, Wiley, New York, 1978, Chapter 9. The photographic materials or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic materials can be coated on a variety of supports as described in Research Disclosure Section XVII and the references described therein.

The photographic materials can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Specific examples of the preparation of compounds of the invention are as follows.

Preparation of
N,N'-Bis(2-gluconamidoethyl)-N,N'-bis nonanoylethylenediamine

This is the compound of formula (1) wherein each Y is —$(CHOH)_4CH_2OH$, each X is —CO—, each R is —$C_8H_{17}$, each n is 2 and m is 2.

Method A

Triethylenetetramine (2.04 g, 14 mmol) and 1,5-D-gluconolactone (5.0 g, 28 mmol) were dissolved in methanol and heated under reflux for 4 h. The solution was cooled and the solvent evaporated under reduced pressure to give N-1-,N-10-triethylenetetraminedigluconamide as a hygroscopic white solid foam.

Found: C, 41.91; H, 7.76; N, 9.36. $C_{18}H_{38}N_4O_{12}$ requires: C, 41.53; H, 7.75; N, 10.76.

Nonanoic acid (3.48 g, 22 mmol) was dissolved in diethyl ether (10 ml) and cooled in an ice bath. Pyridine (2 ml) was added and then ethyl chloroformate (2.3 ml, 24 mmol). After 10 min. the ice bath was removed and after a further 10 min. the mixture was filtered into a solution of N-1-,N-10-triethylenetetraminedigluconamide (5 g, 10 mmol) in methanol at 50° C., washing the residue well with ether. The reaction mixture was heated at 50° C. for 4 h and on cooling a white precipitate formed. This was filtered off and recrystallized from boiling methanol to give N-4,N-7-dinonanoyl-N-1-N-10-triethylenetetramine-digluconamide as a white solid (2.68 g, 34%).

Method B

Gluconolactone (5.34 g, 30 mmol) was dissolved in DMF (60 ml) and a solution of triethylenetetramine (2.34 g, 16 mmol) in DMF added. The solution was heated at 50° C. for 1 h. Meanwhile, nonanoic acid (4.74 g, 30 mmol) and pyridine (2.5 ml) in ether (20 ml) were cooled in an ice bath and ethyl chloroformate (3.26 ml, 34 mmol) added. After 10 min. the ice bath was removed and after a further 10 min. the mixture was filtered directly into the above DMF solution, washing well with ether. The reaction mixture was maintained at 50° C. for 1.5 h, cooled, solvent was evaporated under reduced pressure, and the product isolated by crystallization from methanol (5.28 g, 42%).

Using Method A, compounds wherein each Y is —(CHOH)$_4$CH$_2$OH, each X is —CO—, each n is 2 and m is 2 were prepared. The compounds were those wherein each R was $C_6H_{13}$, $C_7H_{15}$, $C_9H_{19}$, and $C_{12}H_{25}$.

Using Method B, compounds wherein each Y is —(CHOH)$_4$CH$_2$OH, each X is —CO—, each n is 2 and m is 2 were prepared. The compounds were those wherein each R was $C_{14}H_{29}$, $C_{17}H_{35}$, $C_6H_4(CH_2)_4$ and $C_8F_{17}(CH_2)_2$. Additionally, the compound was prepared wherein each Y is —(CHOH)$_5$CH$_2$OH, each X is —CO—, each R is —C$_8$H$_{17}$, each n is 2 and m is 2.

A range of compounds was prepared by linking long chain isocyanates to the intermediate bisgluconamides. This was done in DMF using Method B, with addition of isocyanate instead of mixed anhydride. The compounds prepared were those wherein each Y is —(CHOH)$_4$CH$_2$OH, each X is —NHCO—, each n is 2, m is 2 and each R is $C_8H_{17}$, $C_{12}H_{25}$, $C_{18}H_{37}$ or phenyl.

The invention is further illustrated having regard to the following examples.

EXAMPLE 1

The following data is provided to show the lowering of surface tension provided by compounds of the invention in water at 1% concentration by weight (Table 1) and in a 7% Type IV deionized bone gelatin in water at various concentrations by weight as shown (Table 2).

The compounds are represented by formula 1 wherein each Y is —(CHOH)$_4$CH$_2$OH, each X is —CO—, each n is 2, m is 2 and R is as shown in the Tables.

TABLE 1

| R | Surface Tension mN/m |
|---|---|
| n-C$_7$H$_{15}$ | 35.6 |
| n-C$_8$H$_{17}$ | 34.2 |

TABLE 1-continued

| R | Surface Tension mN/m |
|---|---|
| n-C$_9$H$_{19}$ | 30.9 |

TABLE 2

| R | Surface Tension mN/m Surfactant concentration | | | |
|---|---|---|---|---|
|  | 0.01 | 0.03 | 0.10 | 0.30 |
| n-C$_6$H$_{13}$ | 58.5 | 55.8 | 50.0 | 45.7 |
| n-C$_7$H$_{15}$ | 51.4 | 45.7 | 37.8 | 34.2 |
| n-C$_8$H$_{17}$ | 40.7 | 34.5 | 32.5 | 32.5 |
| n-C$_9$H$_{19}$ | 33.5 | 30.8 | 30.8 | 30.9 |

EXAMPLE 2

Two of the compounds of the invention wherein each Y is —(CHOH)$_4$CH$_2$OH, each X is —CO—, each n is 2, m is 2 and each R is n—C$_8$H$_{17}$ or n—C$_{12}$H$_{25}$, respectively, were each made into a 1% by weight solution or dispersion in water. 10 ml aliquots of the resulting solutions were then mixed with 0.1, 0.5 or 1.0 g of dodecane, or a standard vegetable cooking oil, to give an oil:surfactant ratio of 1:1, 5:1 or 10:1, respectively. After thorough mixing with an ultrasonic microtip for 3 minutes the emulsified mixtures were left to stand. Uniform cloudy emulsions were formed.

EXAMPLE 3

The ability of a compound of the invention to control repellencies caused by an impurity often found in hydrophilic colloid coating compositions was tested as follows.

Two gelatin layers, the uppermost of which contained one of the surfactants listed below in Table 3 as a coating aid, were coated onto a polyethylene terephthalate film base subbed to give good adhesion to gelatin. The bottom layer consisted of a 4% by weight solution of lime-processed bone gelatin in water coated at 85.4 ml/m$^2$. The top layer consisted of a 7% by weight solution of lime-processed bone gelatin in water containing a colored dye marker, 1 ppm oleic acid emulsified in small droplet form to induce repellency, and surfactant at one of the concentrations indicated in Table 3. The top layer was applied at a coverage of 14.2 ml/m$^2$. Both layers were applied simultaneously at a temperature of 40° C. using a conventional double slide hopper with applied suction and a linear coating speed of 15.25 m/min.

TABLE 3

| Concentration (wt %) | R | | |
|---|---|---|---|
|  | n-C$_7$H$_{15}$ | n-C$_8$H$_{17}$ | n-C$_9$H$_{19}$ |
| 0.05 | Rep | C | — |
| 0.10 | C* | C | C |
| 0.20 | C | C | — |

In the above Table, Rep denotes that the coating was covered in many repellencies while C denotes that no repellencies were produced i.e. complete control of repellencies was achieved. C* denotes virtual control of repellencies i.e. only occasional single repellencies were observed, of the order of one or two per meter.

We claim:
1. A silver halide photographic material comprising a support having thereon at least one layer comprising a hydrophilic colloid and a surface active compound having the formula

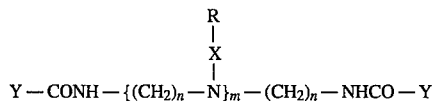

wherein
  each Y independently is a hydrophilic polyhydroxyalkyl group;
  each X independently is

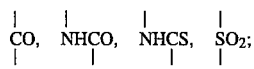

each R independently is a hydrophobic alkyl group or a hydrophobic aryl group;
  each n independently is an integer from 2 to 6; and,
  each m is an integer from 2 to 4.

2. A photographic material according to claim 1 comprising at least one photosensitive silver halide emulsion layer.

3. A photographic material according to claim 1 wherein each Y is —(CHOH)$_y$CH$_2$OH in which y is an integer from 3 to 5.

4. A photographic material according to claim 1 or claim 3 wherein each X is —CO—.

5. A photographic material according to claim 1 or claim 3 wherein the total number of carbon atoms in the R groups does not exceed 24.

6. A photographic material according to claim 1 or claim 3 wherein each R group is an alkyl group having from 4 to 20 carbon atoms.

7. A photographic material according to claim 6 wherein the total number of carbon atoms in the alkyl groups is from 12 to 18.

8. A photographic material according to claim 1 or claim 3 wherein n is 2 or 3.

9. A photographic material according to claim 1 or claim 3 wherein m is 2.

* * * * *